US012616643B2

(12) United States Patent
Kim

(10) Patent No.: US 12,616,643 B2
(45) Date of Patent: May 5, 2026

(54) METHOD OF PREPARING NEW BIOMATERIALS FOR DENTAL PULP REGENERATION AND A COMPOSITION OF NEW BIOMATERIALS PREPARED ACCORDINGLY

(71) Applicant: THE CATHOLIC UNIVERSITY OF KOREA INDUSTRY-ACADEMIC COOPERATION FOUNDATION, Seoul (KR)

(72) Inventor: Sin Young Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 295 days.

(21) Appl. No.: 18/384,188

(22) Filed: Oct. 26, 2023

(65) Prior Publication Data

US 2024/0148614 A1 May 9, 2024

(30) Foreign Application Priority Data

Nov. 3, 2022 (KR) ........................ 10-2022-0145171
Sep. 13, 2023 (KR) ........................ 10-2023-0121994

(51) Int. Cl.
*A61K 6/56* (2020.01)
(52) U.S. Cl.
CPC ..................................... *A61K 6/56* (2020.01)
(58) Field of Classification Search
CPC ..................................................... A61K 6/56
See application file for complete search history.

(56) References Cited

U.S. PATENT DOCUMENTS

2018/0085490 A1* 3/2018 Kay ..................... A61L 24/0005
2022/0273850 A1* 9/2022 About ..................... A61L 27/54

FOREIGN PATENT DOCUMENTS

BR 112019021533 A2 * 5/2020 ............. A61L 27/56
JP 2020-15695 A 1/2020
(Continued)

OTHER PUBLICATIONS

Sara El Moshy et al., "Dental Stem Cell-Derived Secretome/ Conditioned Medium: The Future for Regenerative Therapeutic Applications" Hindawi Stem Cells International, vol. 2020 Article ID 7593402.
(Continued)

*Primary Examiner* — Yogesh P Patel
(74) *Attorney, Agent, or Firm* — Harness, Dickey & Pierce, P.L.C.

(57) ABSTRACT

Proposed are a method of preparing new biomaterials for dental pulp regeneration and a composition of new biomaterials prepared accordingly. The composition of new biomaterials prepared according to the method of preparing new biomaterials for dental pulp regeneration by mixing a first precursor containing calcium silicate-based cement (CSC) at an appropriate concentration and a second precursor containing a secretome of dental pulp-derived mesenchymal stem cells in an appropriate ratio and then drying the resulting mixture under appropriate drying conditions is characterized by further improving the osteogenic differentiation ability of dental pulp stem cells compared to existing materials while maintaining the microhardness of the composition to an appropriate standard. In addition, the composition is advantageous in that an aesthetic effect is excellent by not causing tooth discoloration.

12 Claims, 10 Drawing Sheets

(56)            References Cited

FOREIGN PATENT DOCUMENTS

JP          2020-522536  A      7/2020
JP          2020-527038  A      9/2020
WO      WO2021019096  A1  *   2/2021    ............. A61L 27/56

OTHER PUBLICATIONS

Wu, B. C., et al.; "The effects of calcium silicate cement/fibroblast growth factor-2 composite on osteogenesis accelerator in human dental pulp cells", Journal of Dental Sciences (2014), vol. 10, pp. 145-153.
Bar, J. K., et al.; "Dental Pulp Stem Cell-Derived Secretome and Its Regenerative Potential", International Journal Molecular Sciences (2021), vol. 22, pp. 1-39.
Lee, Y. L., et al.; "Hydration behaviors of calcium silicate-based biomaterials", Journal of the Formosan Medical Association (2017), vol. 116, pp. 424-431.

* cited by examiner

METHOD OF PREPARING NEW BIOMATERIALS FOR DENTAL PULP REGENERATION AND A COMPOSITION OF NEW BIOMATERIALS PREPARED ACCORDINGLY

CROSS REFERENCE TO RELATED APPLICATION

The present application claims priority to Korean Patent Applications 10-2022-0145171, filed Nov. 3, 2022 and No. 10-2023-0121994, filed Sep. 13, 2023, the entire contents of which is incorporated herein for all purposes by this reference.

FIELD

Proposed are a method of preparing new biomaterials for dental pulp regeneration and a composition of new biomaterials prepared accordingly.

BACKGROUND

Dental caries was the second most common disease among teenagers in Korea in 2019, showing a rapidly growing trend with an average annual increase rate of 7.4%. Root canal treatment is often required for advanced dental caries. However, compared to the traditional root canal treatment for permanent teeth that is performed all the way to the root apex, the concept of root canal treatment for immature permanent teeth in adolescence is not well-established. Hence, in the case of immature permanent teeth with an open root apex, research on regenerative root canal treatment is in progress by focusing on the regeneration of the dental pulp and periapical root tissue by performing root canal treatment only on the upper side, allowing stem cells from the apical papilla (SCAP) to be left at the root end.

However, according to recent research on regenerative root canal treatment, in the case of existing materials used in such treatment, complete setting takes a long time. In addition, with longer setting time, the existing materials come into contact with blood or tissue fluids, causing discoloration and thus deteriorating the aesthetic effect. Furthermore, there is a disadvantage leading to a decrease in compressive strength.

DOCUMENT OF RELATED ART

Patent Document (Patent Document 1) Korean Patent Application Publication No. 10-2010-0103821

SUMMARY

Proposed are a method of preparing a composition for dental pulp regeneration by mixing a first precursor containing calcium silicate-based cement (CSC) at an appropriate concentration and a second precursor containing a secretome of dental pulp-derived mesenchymal stem cells and then drying the resulting mixture under predetermined conditions, and a composition for dental pulp regeneration.

A method of preparing new biomaterials for dental pulp regeneration, according to one aspect, includes: preparing a first precursor containing a calcium silicate-based cement (CSC); preparing a second precursor containing a secretome of dental pulp-derived mesenchymal stem cells; preparing a secretome-mixed CSC preliminary composition by mixing the first and second precursors; and drying the preliminary composition.

The CSC may include one or more types selected from the group consisting of Biodentine, RetroMTA, and Endocem MTA Premixed.

The CSC of the first precursor may have a concentration of 3 to 7 mg/mL.

The secretome may have a concentration of 3 to 7 wt % with respect to 100 wt % of the total resulting mixture of the first and second precursors.

The drying of the preliminary composition may be performed for 7 to 9 days.

The drying of the preliminary composition may include: performing primary drying on the preliminary composition at room temperature for 2 to 3 days; and performing secondary drying on the resulting product obtained through the primary drying, at a temperature of 36° C. to 38° C. for 5 to 6 days.

A composition of new biomaterials for dental pulp regeneration, according to another aspect, contains a CSC and a secretome of a dental pulp-derived mesenchymal stem cell, prepared by the method described above.

A composition of new biomaterials prepared according to a method of preparing new biomaterials for dental pulp regeneration from first and second precursors contained in appropriate concentrations by being subjected to appropriate drying conditions is characterized by further improving osteogenic differentiation ability and viability of dental pulp stem cells compared to existing materials while maintaining the hardness of the composition to an appropriate standard. In addition, the composition is advantageous in that an aesthetic effect is excellent without causing tooth discoloration.

DETAILED DESCRIPTION

Figure 1:
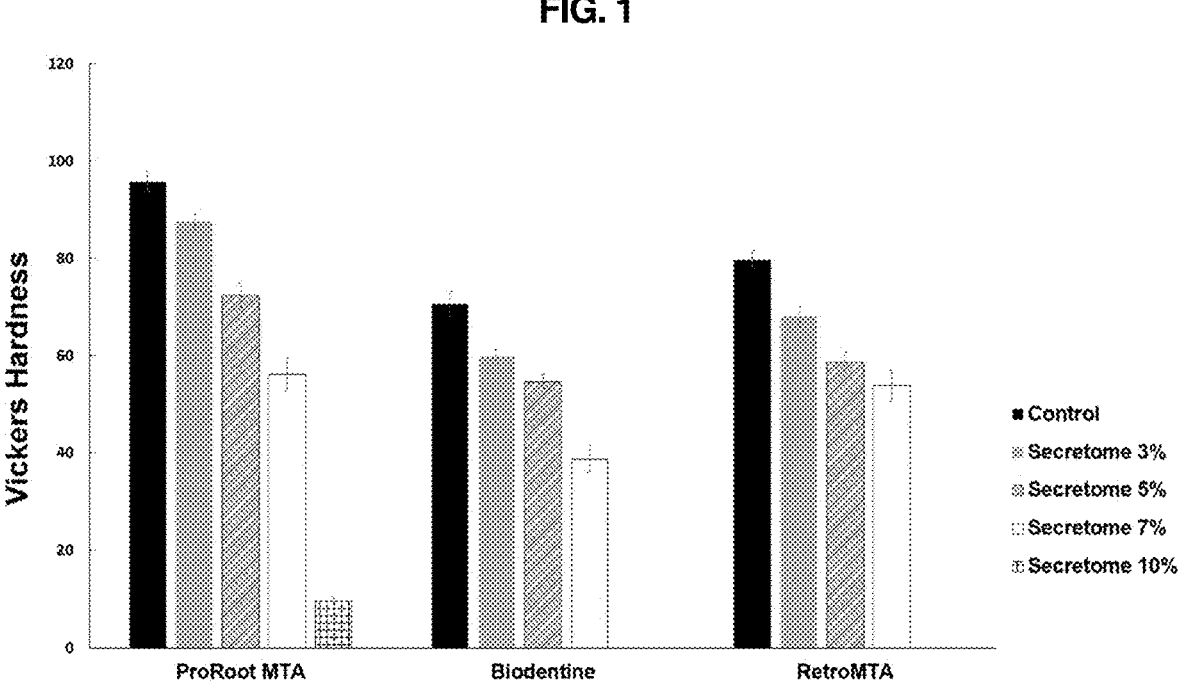
FIG. 1 is a graph showing results of Vickers hardness values of a composition for dental pulp regeneration with varying secretome concentrations of pulp-derived mesenchymal stem cells.

Above objectives, other objectives, features, and advantages of the present disclosure will be readily understood from the following preferred embodiments associated with the accompanying drawings. However, the present disclosure is not limited to the embodiments described herein and may be embodied in other forms. The embodiments described herein are provided so that the disclosure can be made thorough and complete and that the technical spirit of the present disclosure can be fully conveyed to those skilled in the art.

Throughout the drawings, like elements are denoted by like reference numerals. In the accompanying drawings, the dimensions of the structures are larger than actual sizes for clarity of the present disclosure. Terms used in the specification, "first", "second", etc., may be used to describe various components, but the components are not to be construed as being limited to the terms. These terms are used only for the purpose of distinguishing a component from another component. For example, without departing from the scope of the present disclosure, a first component may be referred as a second component, and a second component may be also referred to as a first component. As used herein, the singular forms "a", "an", and "the" are intended to include the plural forms as well unless the context clearly indicates otherwise.

It will be further understood that the terms "comprises", "includes", or "has" when used in this specification specify the presence of stated features, regions, integers, steps, operations, elements, and/or components, but do not preclude the presence or addition of one or more other features, regions, integers, steps, operations, elements, components and/or combinations thereof. It will also be understood that when an element such as a layer, film, area, or sheet is referred to as being "on" another element, it can be directly on the other element, or intervening elements may be present therebetween. Similarly, when an element such as a layer, film, area, or sheet is referred to as being "under" another element, it can be directly under the other element, or intervening elements may be present therebetween.

Unless otherwise specified, all numbers, values, and/or representations that express the amounts of components, reaction conditions, polymer compositions, and mixtures used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In this specification, when a range is described for a variable, the variable will be understood to include all values within the stated range, including the stated endpoints of the range. For example, a range of "5 to 10" includes values of 5, 6, 7, 8, 9, and 10, as well as any subranges such as 6 to 10, 7 to 10, 6 to 9, and 7 to 9. It will be understood to include any value between reasonable integers within the scope of the stated range, such as 5.5, 6.5, 7.5, 5.5 to 8.5, and 6.5 to 9. In addition, for example, a range of "10% to 30%" includes values, such as 10%, 11%, 12%, and 13%, and all integers up to and including 30%, as well as any subranges such as 10% to 15%, 12% to 18%, and 20% to 30%. It will be understood to include any value between reasonable integers within the scope of the stated range, such as 10.5%, 15.5%, and 25.5%.

In the case of mineral trioxide aggregates (MTA), existing materials used in regenerative root canal treatment, complete setting takes a long time. In addition, with longer setting time, the existing material comes into contact with blood or tissue fluids, causing discoloration and thus deteriorating the aesthetic effect. Furthermore, there is a disadvantage leading to a decrease in compressive strength.

Hence, the inventors of the present disclosure conducted intensive research to solve the above problems and found that in the case of a method of preparing new biomaterials for dental pulp regeneration by mixing a first precursor containing calcium silicate-based cement (CSC) at an appropriate concentration and a second precursor containing a secretome of dental pulp-derived mesenchymal stem cells and then drying the resulting mixture under predetermined conditions, and a composition of new biomaterials prepared accordingly, osteogenic differentiation ability and viability of pulp stem cells were further improved compared to those in the case of existing materials while maintaining the hardness of the composition to an appropriate standard. As a result, the present disclosure was completed.

A method of preparing new biomaterials for dental pulp regeneration, according to one aspect of the present disclosure, includes: preparing a first precursor containing a calcium silicate-based cement (CSC); preparing a second precursor containing a secretome of dental pulp-derived mesenchymal stem cells; preparing a preliminary composition by mixing the first and second precursors; and drying the preliminary composition.

According to one embodiment, in the preparing of the first precursor, the first precursor in which the CSC is contained at a predetermined concentration in a medium is prepared.

The term "CSC" used herein may be a biocompatible and bioactive material that has excellent antibacterial properties and excellent mechanical properties and prevents microleakage.

According to one embodiment of the present disclosure, the CSC may include one or more types selected from the group consisting of Biodentine, RetroMTA, and Endocem MTA Premixed. Specifically, a mineral trioxide aggregate (MTA), a hydraulic calcium-silicate cement powder material, is composed of tricalcium silicate, tricalcium aluminate, tricalcium oxide, and other mineral oxides and may be used in various treatments for dental pulp and root canal, such as apexification, apical retrograde filling, pulp revascularization, pulpotomy, direct pulp capping, root perforation repair, and the like. In this case, ProRoot MTA may be prepared by removing iron oxide from gray MTA, which is made of grayish material and contains bismuth oxide for radiopacity in Portland cement, and adding aluminum oxide, magnesium oxide, and iron oxide in amounts significantly smaller than those present in the gray MTA. In addition, Biodentine has better physical properties, easier material handling, and shorter setting time than existing MTAs and may be a dentin restorative material that differentiates dental pulp cells into odontoblast-like cells to stimulate tertiary dentin formation. Furthermore, RetroMTA, a hydraulic calcium zirconium complex, has the following advantages: short setting time, excellent sealability and biocompatibility, and good manipulability by being turned into a gel form during hydration. Endocem MTA Premixed, a material that has been relatively recently developed, contains zirconium dioxide as the main ingredient and is advantageous in that the premixed type enables easy application.

According to one embodiment, the CSC of the first precursor may be contained in a growth medium, specifically, a medium containing Hyclone 10% bovine serum, 100 U/mL penicillin, and 100 μg/mL streptomycin.

According to one embodiment, the CSC contained in the medium of the first precursor may have a concentration of 3 to 7 mg/mL and preferably has a concentration of 4 to 6 mg/mL. When the CSC concentration is excessively low without falling within the concentration range of the CSC, there is a disadvantage leading to deterioration in osteogenic ability, and when the CSC concentration is excessively high, there is a disadvantage leading to an increase in cytotoxicity.

According to one embodiment, in the preparing of the second precursor, the second precursor in which the secretome is contained in a predetermined weight ratio in a growth medium is prepared.

The term "secretome of dental pulp-derived mesenchymal stem cells" used herein means a collection of proteins (secretory proteome) secreted when culturing dental pulp-derived mesenchymal stem cells. In other words, the secretome means a solution obtained by culturing dental pulp-derived mesenchymal stem cells in a serum-free medium and then removing the mesenchymal stem cells therefrom. This solution is rich in proteins, such as various growth factors and cytokines.

The term "mesenchymal stem cell (MSC)" used herein means a multipotent stem cell that maintains self-renewal and stemness and has the ability to be differentiated into various mesodermal cells, for example, various mesenchymal tissues, including bone, cartilage, fat, and muscle cells, or ectodermal cells, including nerve cells. The mesenchymal stem cell may be derived from the umbilical cord, cord blood, bone marrow, fat, muscle nerves, skin, amniotic membrane, chorion, decidua, placenta, and the like. In addition, the mesenchymal stem cell may be derived from humans, fetuses, or non-human mammals.

According to one embodiment, in the mixing method to prepare the preliminary composition, the second precursor is mixed in the first precursor using a pipette to prepare a CSC eluate in which the secretome is mixed in an appropriate ratio.

According to one embodiment, the secretome contained in the secretome-containing CSC eluate may have a concentration of 3 to 7 wt % and preferably has a concentration of 4 to 6 wt %, with respect to 100 wt % of the total resulting mixture of the first and second precursors. When the secretome concentration is excessively low without falling within the concentration range of the secretome, there is a disadvantage leading to a deterioration in the degree of improving osteogenic ability, and when the secretome concentration is excessively high, there is a disadvantage leading to a decrease in the microhardness of the secretome-containing CSC mixture.

A composition of new biomaterials for dental pulp regeneration, according to another aspect, contains a calcium silicate-based cement (CSC) and a secretome. In this case, the description related to the composition of new biomaterials for dental pulp regeneration that are redundant with the description described in the method of preparing new biomaterials for dental pulp regeneration may be omitted. When preparing the secretome-mixed composition for dental pulp regeneration, a solution in which CSC powder is mixed in distilled water or calcium chloride is mixed and set according to the manufacturer's instructions. In this process, the secretome solution is mixed at an appropriate concentration of 3 to 7 wt % with respect to 100 wt % of the preliminary composition.

According to one embodiment, in the drying of the preliminary composition, the preliminary composition is dried to prepare the composition of new biomaterials having a final desired form, such as a pellet.

According to one embodiment, the drying of the preliminary composition may be performed for 7 to 9 days, and preferably includes: performing primary drying on the preliminary composition at room temperature for 2 to 3 days; and performing secondary drying on the resulting product obtained through the primary drying, at a temperature of 36° C. to 38° C. for 5 to 6 days.

Specifically, the primary drying is performed at room temperature of 23° C. to 27° C. for 2 to 3 days to obtain a primarily set cement. When performing the primary drying at an excessively low temperature without falling within the temperature condition range of the primary drying, there is a possibility that the cement is incompletely set, and when performing the primary drying at an excessively high temperature, there is a disadvantage in that the cement working time is shortened. In addition, when performing the primary drying for an excessively short time, there is a disadvantage leading to a decrease in the microhardness, and when performing the primary drying for an excessively long time, there is a possibility of airborne contamination.

In addition, the secondary drying is performed at a temperature of 36° C. to 38° C. for 5 to 6 days to obtain a completely set cement.

In other words, the composition of new biomaterials prepared according to the method of preparing new biomaterials for the dental pulp regeneration by mixing the first precursor containing the calcium silicate-based cement (CSC) at an appropriate concentration and the second precursor containing the secretome in an appropriate ratio and then drying the resulting mixture under appropriate conditions is advantageous in further improving the osteogenic differentiation ability of dental pulp stem cells and maintaining the microhardness of the composition at an appropriate standard, compared to existing materials.

Hereinafter, the present disclosure will be described in more detail through examples. However, the following examples are disclosed for illustrative purposes, and the scope of the present disclosure is not limited by the following examples.

Preparation Example 1: Preparation of Secretome of Dental Pulp-Derived Mesenchymal Stem Cells 1-1. Obtaining of Dental Pulp-Derived Mesenchymal Stem Cells Dental pulp was extracted from a shed permanent tooth, reacted with collagenase (3 mg/mL) and dispase (4 mg/mL) at 37° C. for 1 hour, and then allowed to pass through a 70-μm cell strainer to isolate each cell. After inactivating the enzymes using aMEM containing 10% FBS, the isolated cells were transferred to a culture medium containing aMEM, 50 μg of ascorbic acid, 10 ng of basic fibroblast growth factor (bFGF), 1% penicillin-streptomycin, or amphotericin B, and then cultured in a 5% $CO_2$ incubator under the following conditions: a humidity of about 90% and a temperature of about 37° C.

Subculture was performed as follows: washing a culture medium-free flask with phosphate-buffered solution, dropping the cells with 0.25% Trypsin-EDTA (GIBCO), centrifuging the cell suspension, and then measuring the number of cells and testing viability, followed by performing subculture again 3 times. The medium used for the subculture was aMEM supplemented with 50 μg of ascorbic acid, 10 ng of bFGF, 10% FBS, 1% penicillin-streptomycin, or amphotericin B as an antifungal agent.

When the cells reached a confluency of about 70% to 80%, the culture medium was removed from the culture using a pipette, washed twice with phosphate buffer solution, added to a serum-free medium (aMEM supplemented with 50 μg of ascorbic acid, 10 ng of bFGF, 1% penicillin-streptomycin, or amphotericin B as an antifungal agent), and cultured for 48 hours in a 5% $CO_2$ incubator under the following conditions: a humidity of about 90% and a temperature of about 37° C.

1-2. Preparation of Secretome

After culturing $2\times10^6$ to $5\times10^6$ cells of the dental pulp-derived stem cells (DPSCs) obtained in Preparation Example 1-1 in a serum-free medium (aMEM supplemented with 50 μg of ascorbic acid, 10 ng of bFGF, 1% penicillin-streptomycin, or amphotericin B as an antifungal agent), 50 mL of the culture medium cultured in the serum-free medium (conditioned medium) was centrifuged at 1500 rpm for 5 minutes. Then, the supernatant was transferred to a new tube, centrifuged at 3000 rpm for 3 minutes, followed by removing residues of the suspension, and left at –20° C. for 1 hour by adding 100% ethanol. Next, the resulting product was centrifuged at 15000 rpm at 4° C. for 15 minutes. Thereafter, the precipitate was treated with 90% ethanol once again, washed with salts, and then centrifuged at 15,000 rpm for 7 minutes. After discarding the ethanol supernatant using a pipette, 2.5 mL of water for injection was dispensed in an amount of 500 μL into each 1.8-mL tube, and the tubes were left in a defreezer at –80° C. for 3 hours. Afterward, freeze-drying was performed for 8 hours to prepare a powder form.

Preparation Example 2: Preparation of Preliminary Composition of New Biomaterials to Examine Osteogenic Differentiation Ability A first precursor containing a CSC at a concentration of 5 mg/mL was prepared in a growth medium containing Hyclone 10% bovine serum, 100 U/mL penicillin, and 100 μg/mL streptomycin. In addition, a second precursor containing the secretome in an appropriate weight ratio was prepared in the growth medium. Then, the second precursor was mixed with the first precursor using a pipette to prepare a secretome-mixed preliminary composition (CSC eluate) containing the second precursor at a concentration of 5 wt % with respect to 95 wt % of the first precursor.

Example 1: Examination of Microhardness of New Biomaterials for Dental Pulp Regeneration with Varying Secretome Concentrations According to Preparation Example 2, a composition for dental pulp regeneration was prepared using an existing material, mineral trioxide aggregate (ProRoot MTA), or other types of CSC (Biodentine and RetroMTA) with varying secretome concentrations. Then, after performing Vicker's hardness test (traces created when applying a load (P) of 0.02 kgf to the composition for dental pulp nerve regeneration), the Vickers hardness (Hv) was measured to evaluate the microhardness, the basic requirement for dental materials to resist masticatory pressure. FIG. 1 shows the results thereof.

FIG. 1 is a graph showing the results of the Vickers hardness values of new biomaterials with varying secretome concentrations.

Referring to FIG. 1, it was confirmed that the higher the secretome concentration, the lower the microhardness of new biomaterials. In particular, even in the case of containing other types of CSC, when the secretome concentration was 10%, all the hardness values were reduced. In addition, in the case of using Biodentine and RetroMTA, hardness failed to be measured, which was immeasurable. In other words, it was confirmed that the minimum hardness was satisfied only when the secretome concentration was at least 7%.

Example 2: Examination of Conditions to Increase Microhardness of the Composition of New Biomaterials for Dental Pulp Regeneration A composition of new biomaterials was prepared according to Preparation Example 2, except for performing primary drying at room temperature for 3 days. The results of measuring Vickers hardness values as in Example 1 are shown in FIG. 2.

Figure 2:
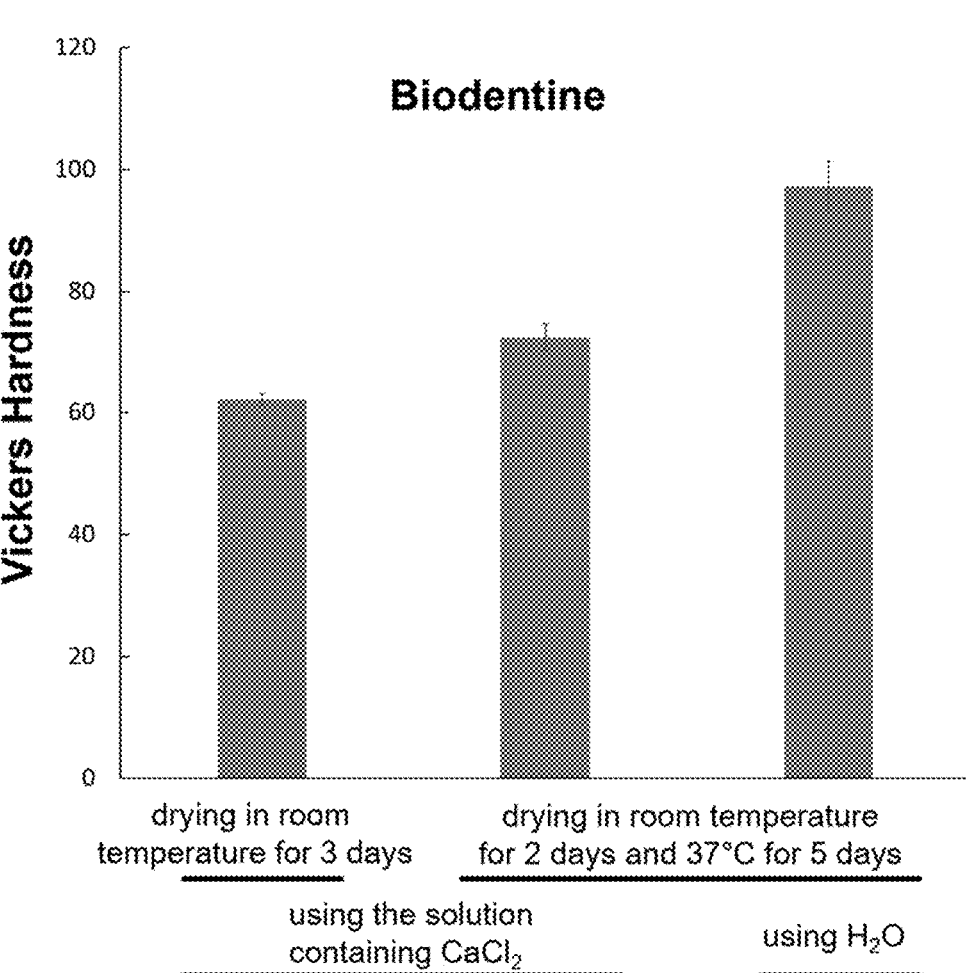
FIG. 2 is a graph showing results of Vickers hardness values of a composition for dental pulp regeneration with varying drying conditions.

Specifically, FIG. 2 is a graph showing the results of Vickers hardness values of the composition of new biomaterials with varying drying conditions.

Referring to FIG. 2, it was confirmed that the hardness in the case of both the compositions of new biomaterials prepared through the primary drying and secondary drying was superior to that in the case of the composition of new biomaterials prepared through the primary drying for only 3 days at room temperature. In addition, it was confirmed that the microhardness of the composition of new biomaterials was more improved when using water ($H_2O$) as the solvent than when using the solution containing calcium chloride. When using the solvent containing calcium chloride, even though there may be an advantage in shortening the setting time of the composition of new biomaterials, there is a disadvantage leading to a decrease in the hardness of the prepared product compared to when mixing distilled water.

Figure 4:
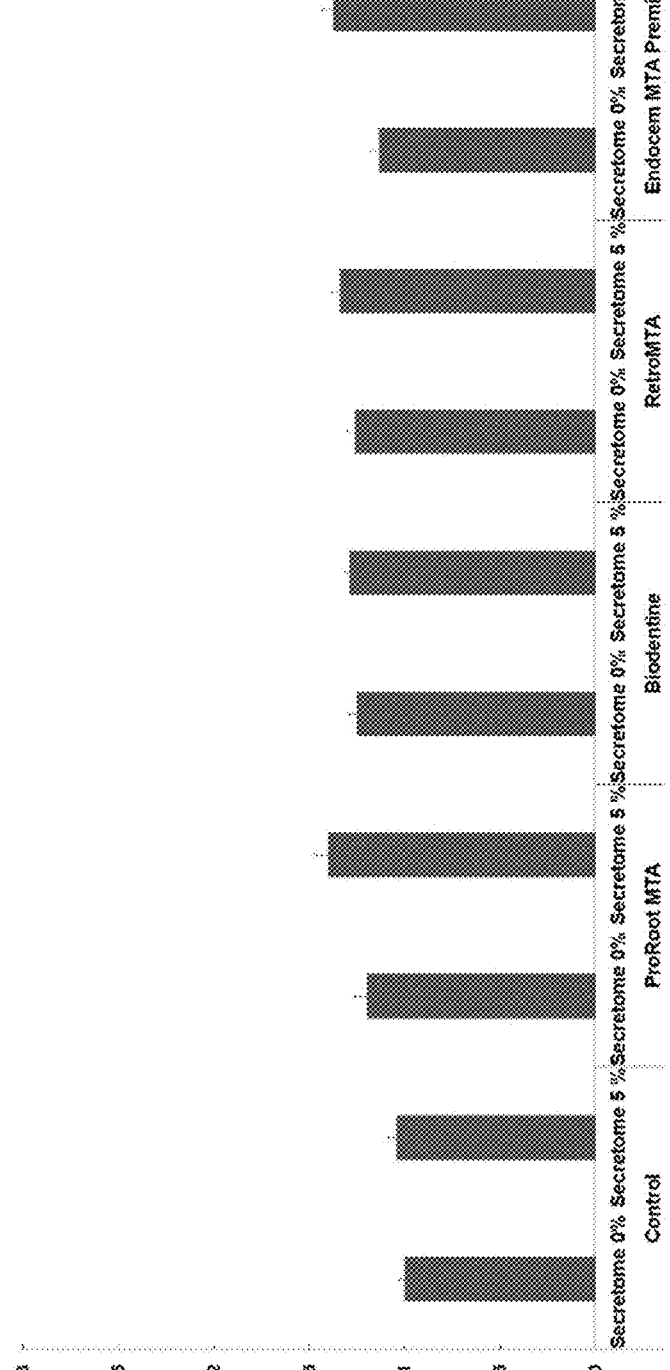
FIG. 4 is a graph showing measurement results of the amount of alkaline phosphatase on Day 3 in dental pulp stem cells when adding a composition for dental pulp regeneration.
Figure 5:
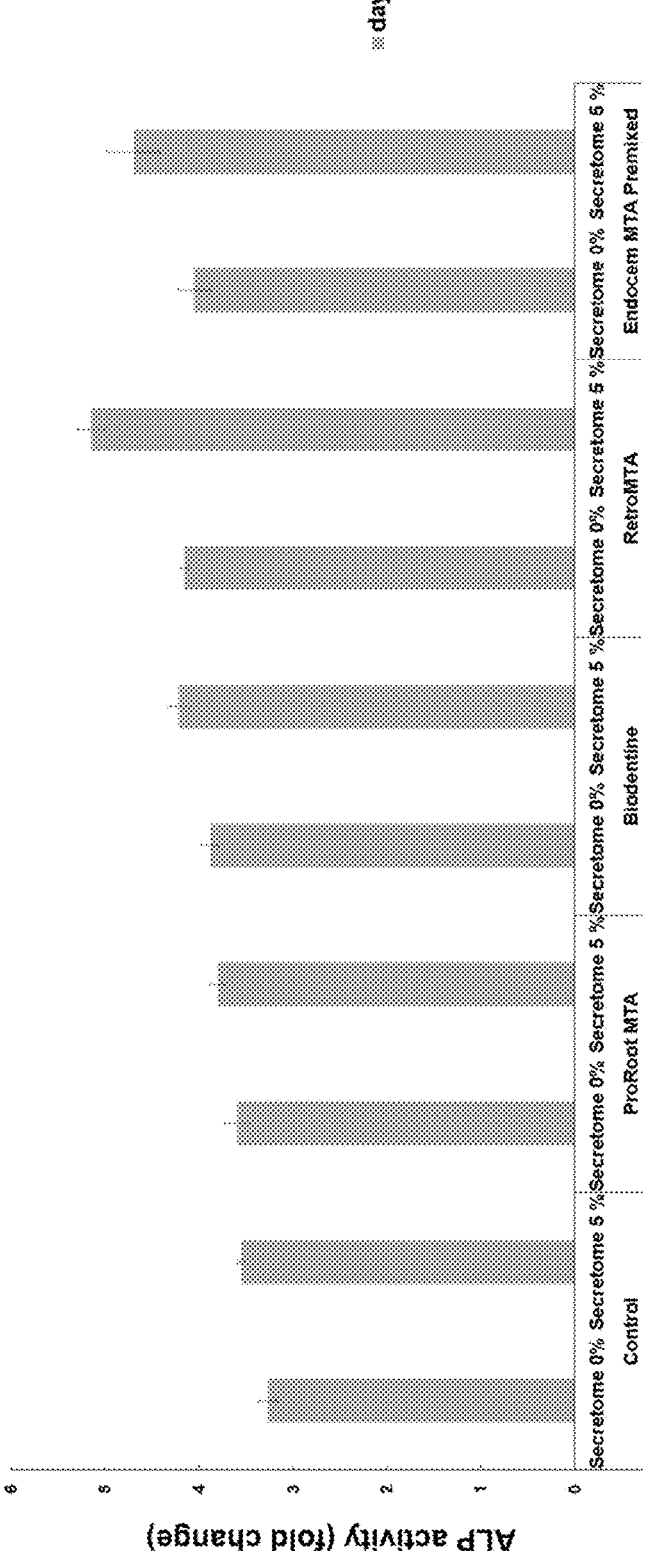
FIG. 5 is a graph showing measurement results of the amount of alkaline phosphatase on Day 6 in dental pulp stem cells when adding a composition for dental pulp regeneration.

Example 3: Examination of Alkaline Phosphatase Activity of Secretome-Mixed CSC Eluate According to Preparation Example 2, a secretome-mixed CSC eluate was prepared using an existing material, mineral trioxide aggregate (ProRoot MTA), or other types of CSC (Biodentine, RetroMTA, and Endocem MTA Premixed) with the fixed secretome concentration of 5%. Then, the secretome-mixed CSC eluate was added to human dental pulp stem cells to measure the amount of alkaline phosphatase serving to differentiate osteoblasts in the dental pulp stem cells, thereby evaluating the osteogenic differentiation ability of the dental pulp stem cells. The results thereof are shown in FIGS. 3, 4, and 5.

Figure 3:
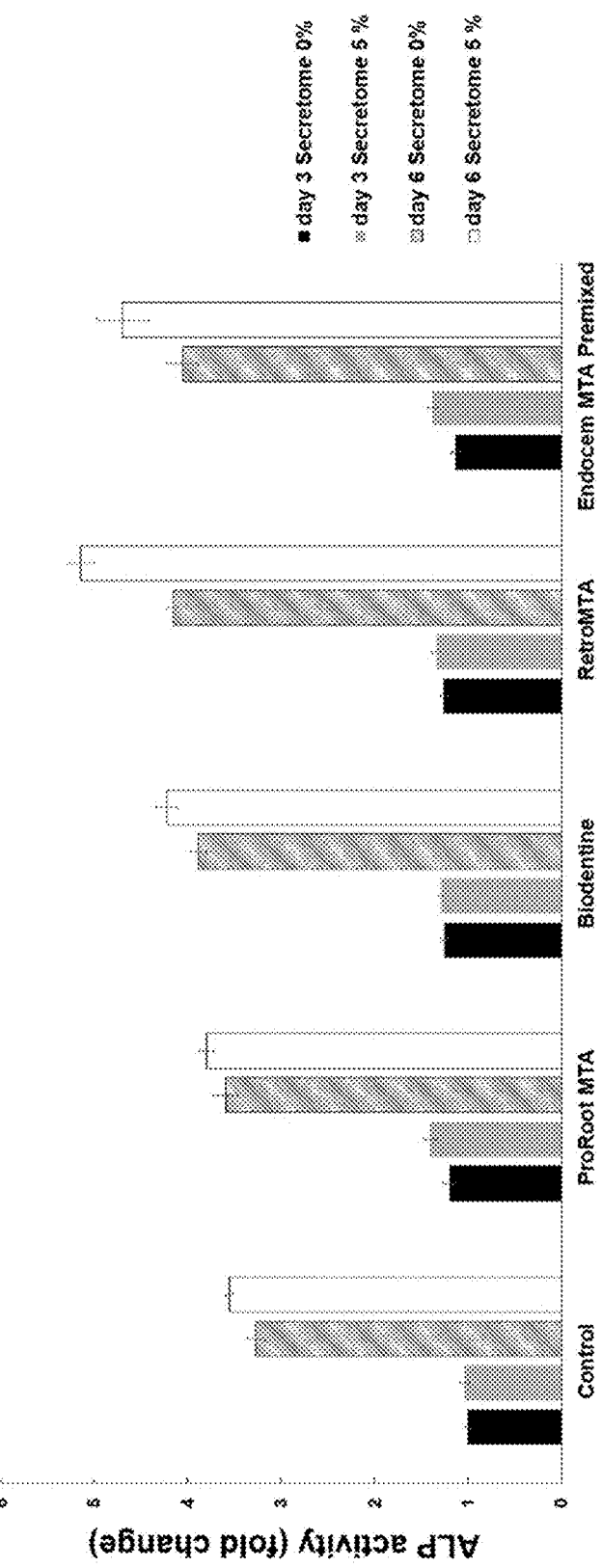
FIG. 3 is a graph showing measurement results of the total amount of alkaline phosphatase (Days 3 and 6) in dental pulp stem cells when adding a composition for dental pulp regeneration.

Specifically, FIG. 3 is a graph showing the measurement results of alkaline phosphatase activity in the dental pulp stem cells when adding the composition of new biomaterials prepared accordingly. FIG. 4 is a graph showing the measurement results of alkaline phosphatase activity on Day 3, and FIG. 5 is a graph showing the measurement results of alkaline phosphatase activity on Day 6.

Referring to FIG. 3, it was confirmed that the osteogenic differentiation ability of the secretome-mixed CSC eluates prepared by using each of all the types of CSC was superior to that of each group of the eluates prepared without secretome. In addition, it was confirmed that the alkaline phosphatase activity was higher on Day 6 than on Day 3. Referring to FIG. 4, there was no significant difference between the secretome-mixed CSC eluate and the secretome-free CSC eluate on Day 3. However, referring to FIG. 5, there was a significant difference between the secretome-mixed CSC eluate and the secretome-free CSC eluate on Day 6. In particular, it was confirmed that the alkaline phosphatase activity was the highest in the case of the secretome-mixed CSC eluate prepared using RetroMTA and Endocem MTA Premixed.

Figure 6:
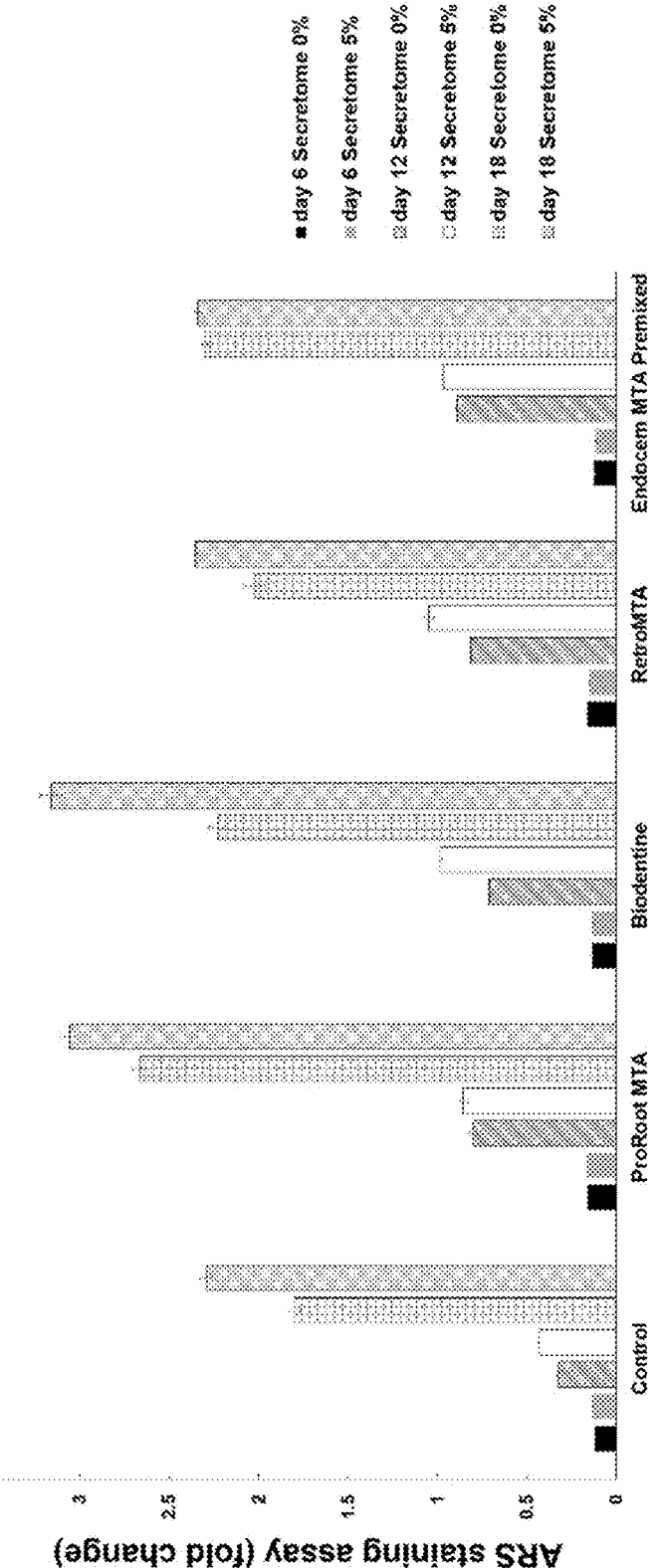
FIG. 6 is a graph showing measurement results of the total amount of calcium crystallization formed (Days 6, 12, and 18) in dental pulp stem cells when adding a composition for dental pulp regeneration.
Figure 7:
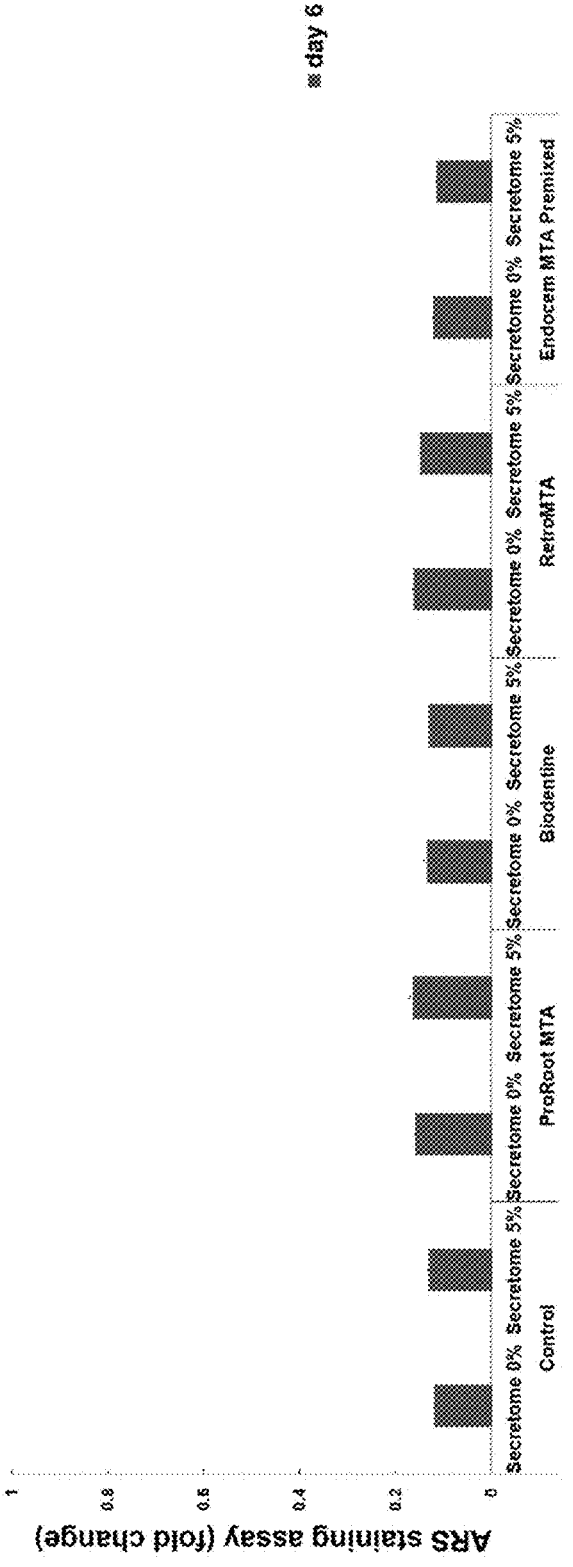
FIG. 7 is a graph showing measurement results of the amount of calcium crystallization formed on Day 6 in dental pulp stem cells when adding a composition for dental pulp regeneration.
Figure 8:
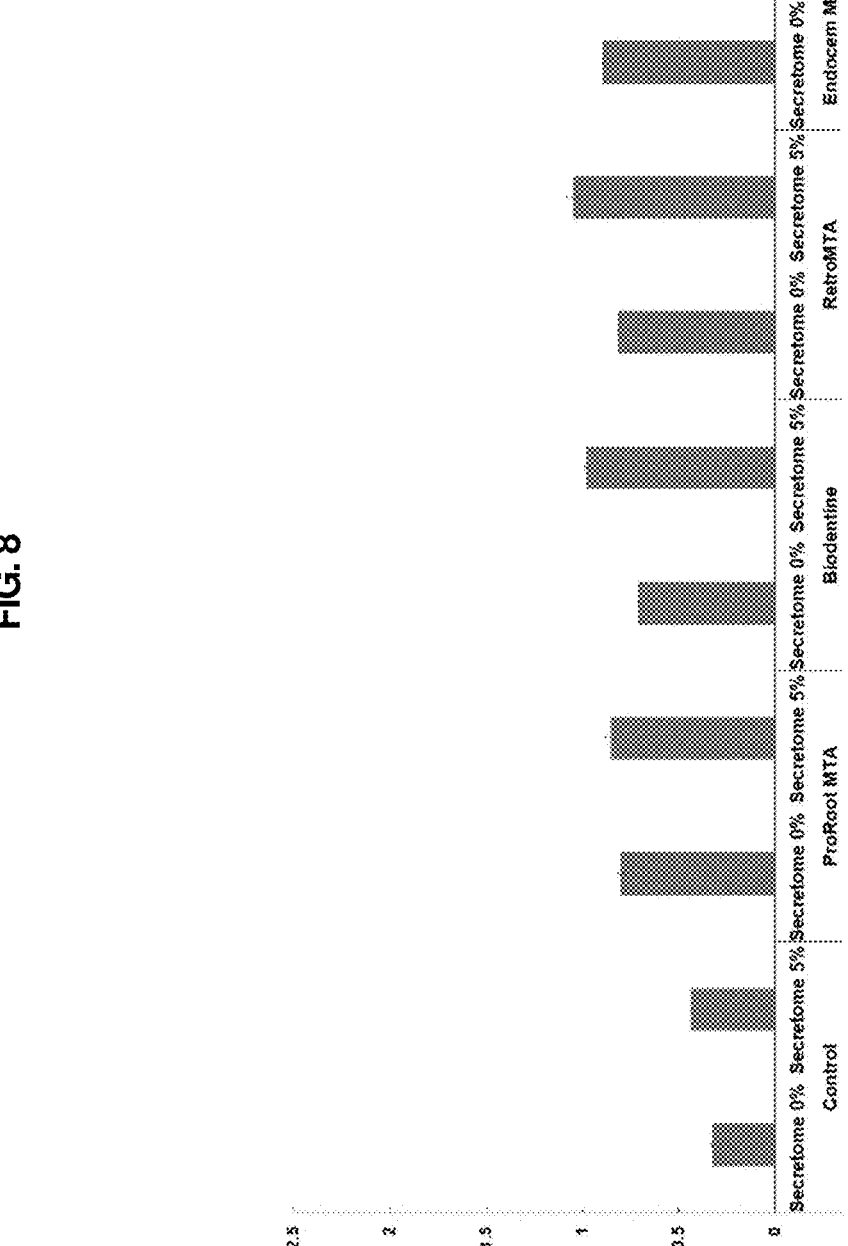
FIG. 8 is a graph showing measurement results of the amount of calcium crystallization formed on Day 12 in dental pulp stem cells when adding a composition for dental pulp regeneration.
Figure 9:
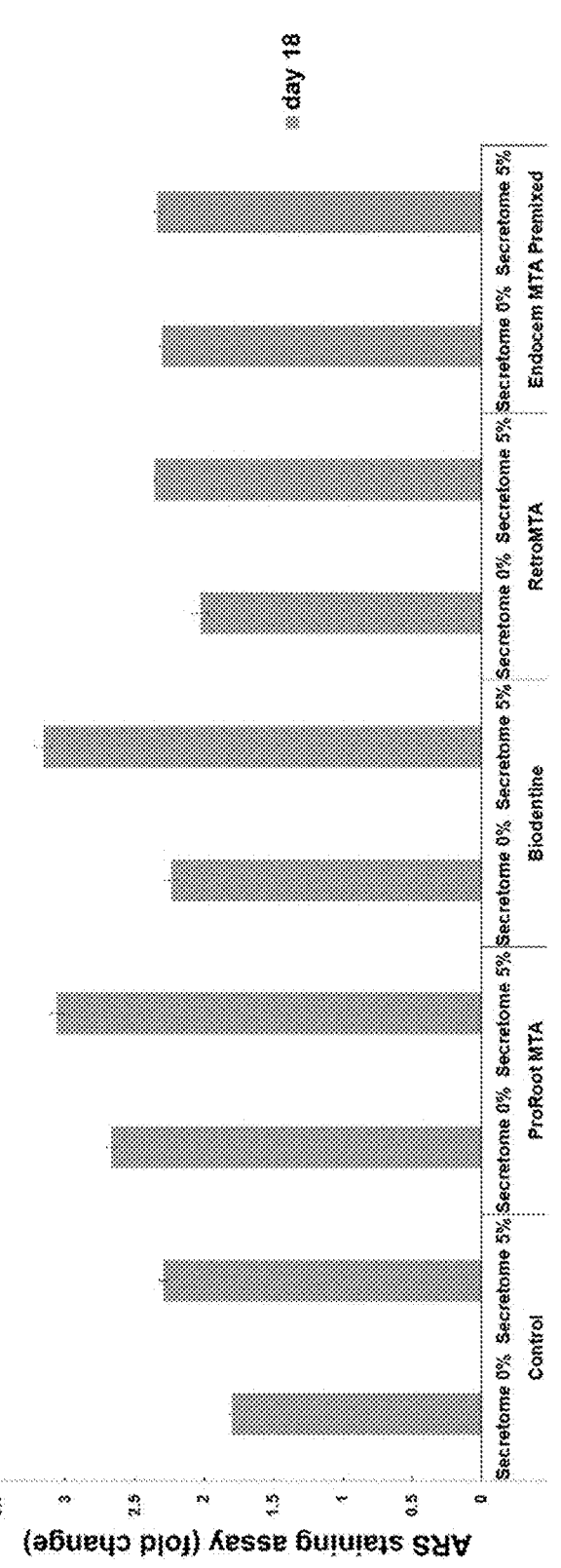
FIG. 9 is a graph showing measurement results of the amount of a calcium crystallization formed on Day 18 in dental pulp stem cells when adding a composition for dental pulp regeneration.
Figure 10:
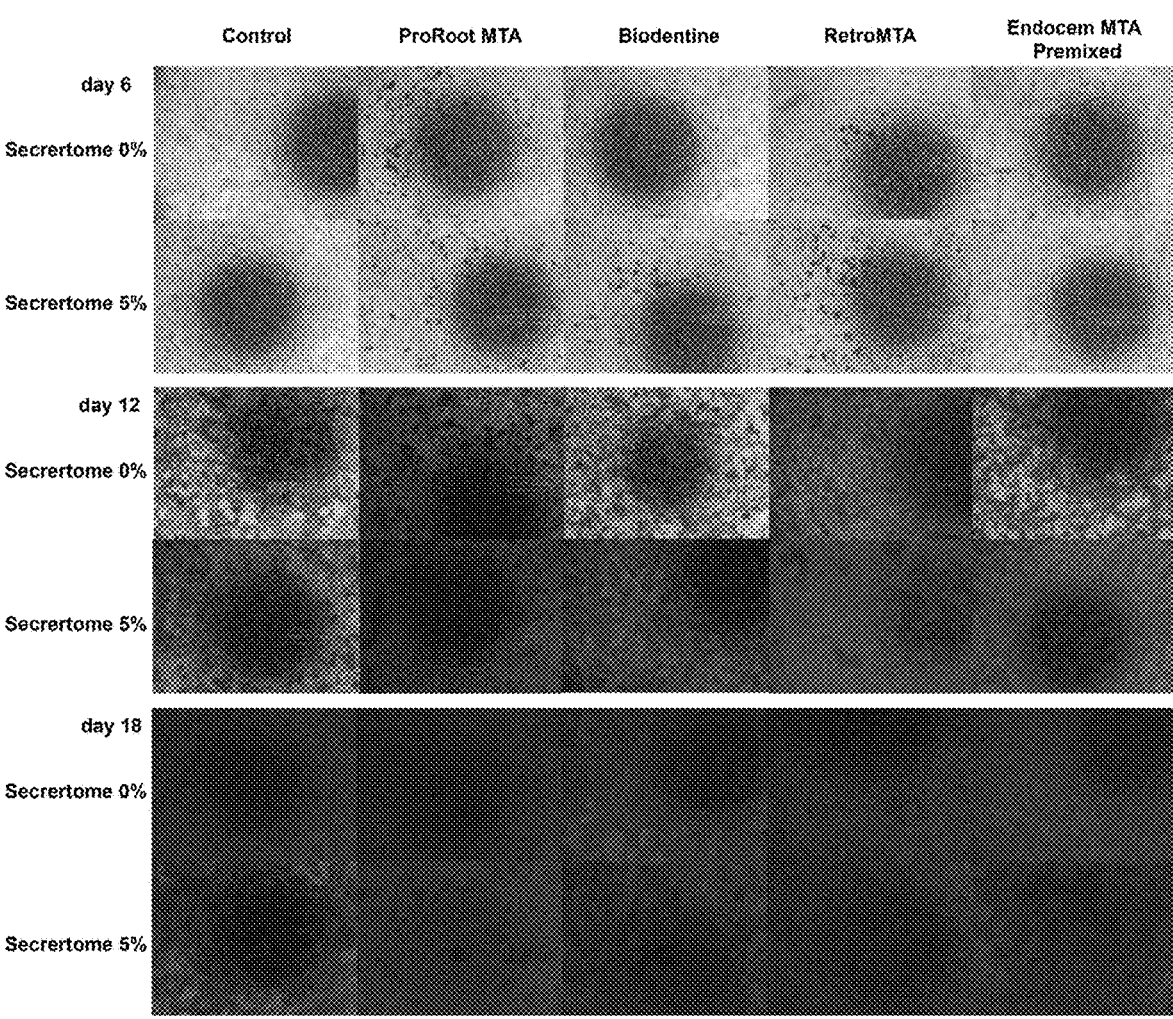
FIG. 10 is a representative image of the entire calcium crystallization formed (on Days 6, 12, and 18) in dental pulp stem cells when adding a composition for dental pulp regeneration.

Example 4: Examination of Calcium Crystal Formation Ability of Secretome-Mixed CSC Eluate According to Preparation Example 2, a secretome-mixed CSC eluate was prepared using an existing material, mineral trioxide aggregate (ProRoot MTA), or other types of CSC (Biodentine, RetroMTA, and Endocem MTA Premixed) with the fixed secretome concentration of 5%. Then, the secretome-mixed CSC eluate was added to human dental pulp stem cells to evaluate the ability of the stem cells to directly form calcium crystals using alizarin red S staining. The results thereof are shown in FIGS. 6, 7, 8, 9, and 10. Referring to FIG. 6, it was confirmed that the osteogenic differentiation ability of the secretome-mixed CSC eluates prepared by using each of all the types of CSC was superior to that of each group of the eluates prepared without secretome. In addition, it was confirmed that the osteogenic differentiation ability was better on Day 12 than on Day 6 and Day 18 than on Day 12. Referring to FIG. 7, there was no significant difference in the ability to form calcium crystals between the secretome-mixed CSC eluate and the secretome-free CSC eluate on Day 6. However, referring to FIG. 8, there was a significant difference in the ability to form calcium crystals between the secretome-mixed CSC eluate and the secretome-free CSC eluate on Day 12. In addition, referring to FIG. 9, there was an even more significant difference in the ability to form calcium crystals between the secretome-mixed CSC eluate and the secretome-free CSC eluate on Day 18. In particular, it was confirmed that the ability to form calcium crystals was the best in the case of the secretome-mixed CSC eluates prepared using Biodentine, similar to the group prepared using ProRoot MTA. Referring to FIG. 10, it was confirmed that the alizarin red S staining results of all the secretome-mixed CSC eluates, including the control group and the ProRoot MTA group, showed darker colors. In addition, it was observed that as time elapsed, i.e., after Days 6, 12, and 18, the degree of staining gradually became darker.

What is claimed is:

1. A method of preparing new biomaterials for dental pulp regeneration, the method comprising:
   preparing a first precursor comprising a calcium silicate-based cement (CSC);
   preparing a second precursor comprising a secretome of a pulp-derived mesenchymal stem cell;
   preparing a secretome-mixed CSC preliminary composition by mixing the first and second precursors; and
   drying the preliminary composition.

2. The method of claim 1, wherein the CSC comprises one or more types selected from the group consisting of dentin restorative material, hydraulic calcium zirconium complex, and premixed mineral trioxide aggregate.

3. The method of claim 1, wherein the CSC of the first precursor has a concentration of 3 to 7 mg/mL.

4. The method of claim 1, wherein the secretome has a concentration of 3 wt % to 7 wt % with respect to 100 wt % of the total resulting mixture of the first and second precursors.

5. The method of claim 1, wherein the drying of the preliminary composition is performed for 7 to 9 days.

6. The method of claim 5, wherein the drying of the preliminary composition comprises:
   performing primary drying on the preliminary composition at room temperature for 2 to 3 days; and
   performing secondary drying on the resulting product obtained through the primary drying, at a temperature of 36° C. to 38° C. for 5 to 6 days.

7. A composition of new biomaterials for dental pulp regeneration, the composition prepared by the method of claim 1.

8. The composition of claim 7, wherein the CSC comprises one or more types selected from the group consisting of dentin restorative material, hydraulic calcium zirconium complex, and premixed mineral trioxide aggregate.

9. The composition of claim 7, wherein the CSC of the first precursor has a concentration of 3 to 7 mg/mL.

10. The composition of claim 7, wherein the secretome has a concentration of 3 wt % to 7 wt % with respect to 100 wt % of the total resulting mixture of the first and second precursors.

11. The composition of claim 7, wherein the drying of the preliminary composition is performed for 7 to 9 days.

12. The composition of claim 11, wherein the drying of the preliminary composition comprises:
   performing primary drying on the preliminary composition at room temperature for 2 to 3 days; and
   performing secondary drying on the resulting product obtained through the primary drying, at a temperature of 36° C. to 38° C. for 5 to 6 days.

* * * * *